United States Patent [19]

Hille et al.

[11] Patent Number: 5,391,375

[45] Date of Patent: Feb. 21, 1995

[54] TRANSDERMAL THERAPEUTICAL SYSTEM WITH PHYSOSTIGMINE AS ACTIVE COMPONENT AND PROCESS FOR THE PRODUCTION THEREOF

[75] Inventors: Thomas Hille; Hans-Rainer Hoffmann, both of Neuwied; Hans-Joachim Huber; Axel Knoch, both of Munich; Gerhard Schneider, Baldham; Fritz Stanislaus, Munich, all of Germany

[73] Assignees: LTS Lohmann Therapie-Systeme GmbH & Co., KG, Neuwied; Klinge Pharma GmbH, Munich, both of Germany

[21] Appl. No.: 76,682

[22] Filed: Apr. 26, 1993

Related U.S. Application Data

[63] Continuation of Ser. No. 727,324, Mar. 3, 1991, abandoned, which is a continuation of Ser. No. 452,530, Dec. 18, 1989, abandoned.

[30] Foreign Application Priority Data

Dec. 22, 1988 [DE] Germany ............................. 3843238

[51] Int. Cl.$^6$ ............................................. A61F 13/02
[52] U.S. Cl. ..................................... 424/449; 424/448; 424/485; 424/486; 424/487
[58] Field of Search .................. 424/449, 448, 485–487

[56] References Cited

U.S. PATENT DOCUMENTS

| | | | |
|---|---|---|---|
| 3,996,934 | 12/1976 | Zaffaroni | 424/449 |
| 4,668,506 | 5/1987 | Bawa | 424/449 |
| 4,765,985 | 8/1988 | Leeson | 424/449 |
| 4,788,063 | 11/1988 | Fisher | 424/449 |
| 4,917,676 | 4/1990 | Heiber et al. | 424/449 |
| 5,089,267 | 2/1992 | Hille | 424/449 |

FOREIGN PATENT DOCUMENTS 0156080 12/1984 European Pat. Off. .

OTHER PUBLICATIONS

Drora Levy, "A Novel Transdermal Therapeutic System as a Potential Treatment for Alzheimer's Disease," in *Adv. Behav. Biol.*, 1986, pp. 567–563.

*Primary Examiner*—D. Gabrielle Phelan
*Attorney, Agent, or Firm*—Sprung Horn Kramer & Woods

[57] ABSTRACT

The present invention relates to a transdermal therapeutical system for the administration of physostigmine to the skin via a backing layer which is impermeable to active substances, an active substance deposit comprising at least one auxiliary agent with supporting and distributing function in the form of a textile fabric material, a matrix surrounding said deposit from all sides, and optionally a removable protective layer, the matrix of which comprises 10–90%-wt polymeric material selected from the group consisting of polymers on the basis of acrylate and/or methacrylate and esters of hydrogenated colophonium, 0–30%-wt softener on the basis of hydrocarbons and/or esters, and that the active substance deposit immediately after its production comprises 15–85%-wt of a 0.1–70%-wt physostigmine solution.

15 Claims, 3 Drawing Sheets

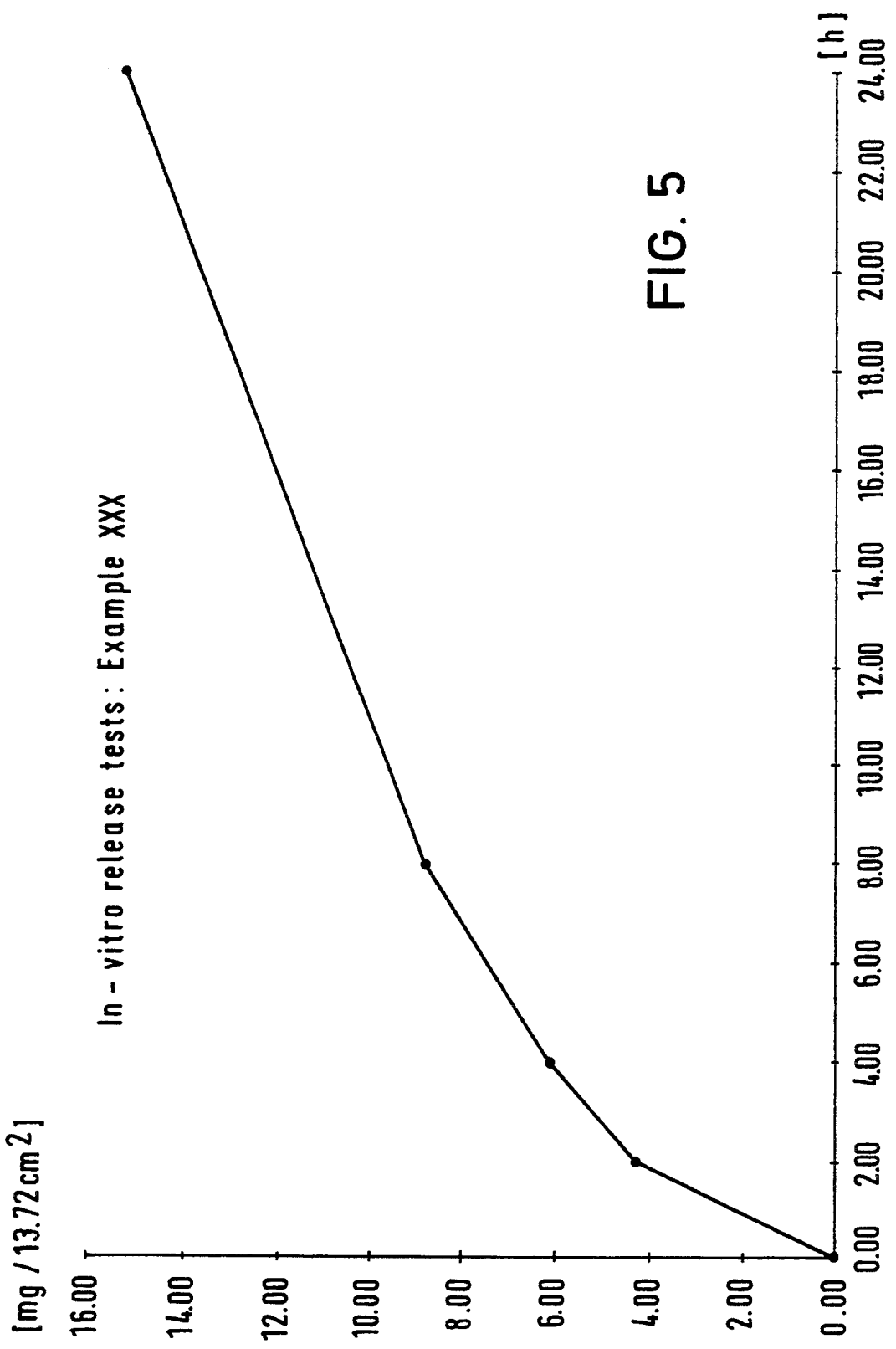

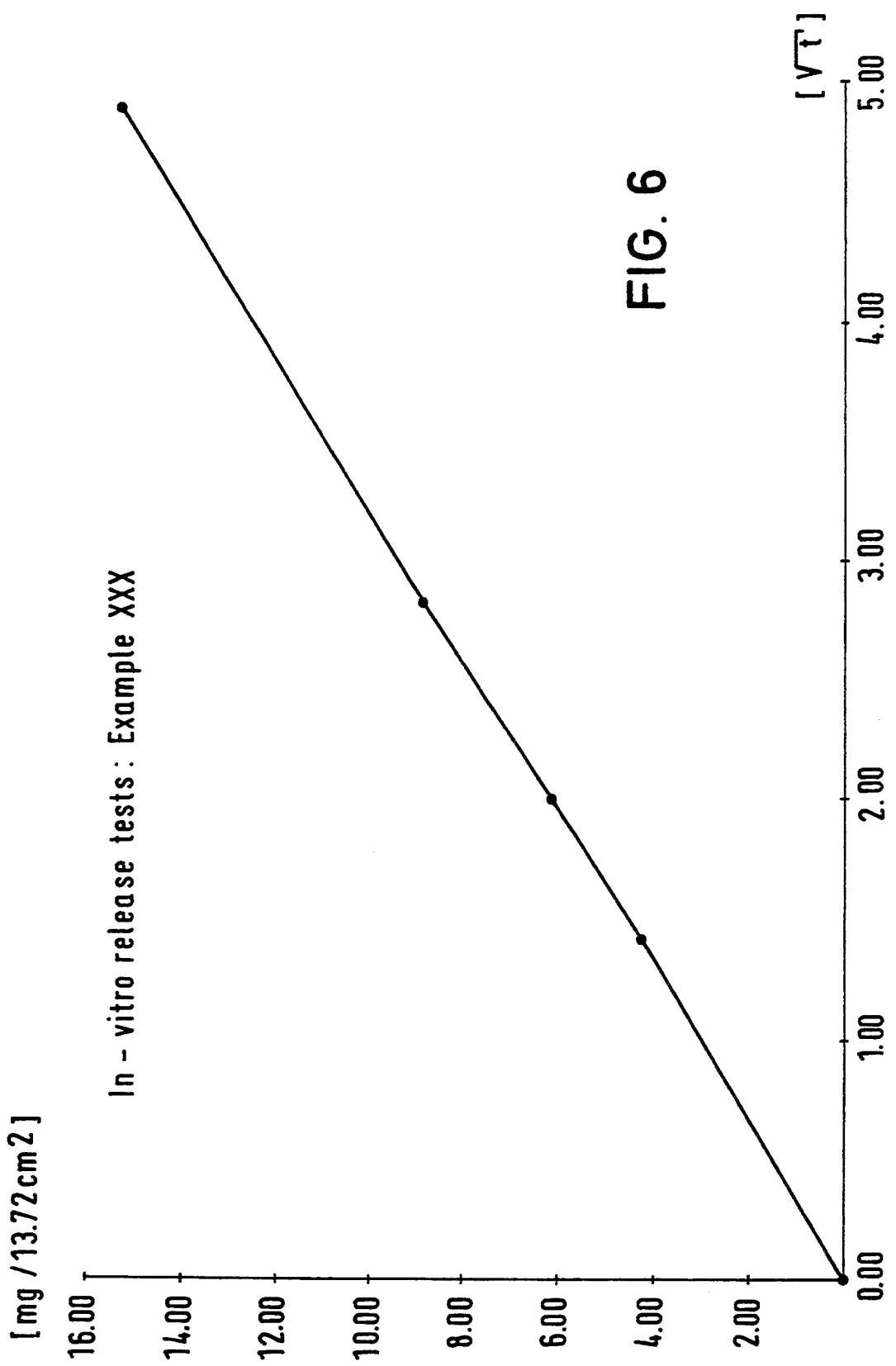

TRANSDERMAL THERAPEUTICAL SYSTEM WITH PHYSOSTIGMINE AS ACTIVE COMPONENT AND PROCESS FOR THE PRODUCTION THEREOF

This application is a continuation of application Ser. No. 727,324, filed Mar. 3, 1991, now abandoned, which is a continuation of application Ser. No. 452,530, filed Dec. 18, 1989, now abandoned.

DESCRIPTION

The present invention relates to a transdermal therapeutical system comprising physostigmine as active component, and to a process for its production.

The application of physostigmine for the treatment of the Alzheimer disease is described in literature, whereby the efficiency of the substance has been judged differently by different authors. Since the alkaloid exhibits a high first pass effect - the bioavailability of physostigmine after oral administration is in the range of 5% - the differing results must be attributed to different forms of application.

DE-OS 35 28 979 describes a composition which in addition to physostigmine comprises a carboxylic acid of medium chain length; this composition may be applied on a bandage, an insert, or a compress, which are applied by means of a dressing. This kind of application is no therapeutical system per se; thus it is intended to provide the bandage, compress, or insert with an inner reservoir layer, an impermeable protective blocking foil, or an impermeable protective film and to apply a diffusion con-trolling membrane between the reservoir and the skin, which is not described in detail. Neither the diffusion controlling membrane nor the protective foils are described more precisely. The carboxylic acids are explicitly mentioned to be effective carriers for the administration of the pharmaceutical through the skin which otherwise could not penetrate through the barrier of the skin. However, this statement is not tenable from the scientific point of view.

DE-PS 36 06 892 describes a retarded application of physostigmine and other active substances, which may be carried out transdermally. A special formulation is not disclosed. What is more, it is hinted at a pre-described formulation (US-PS 3,921,363).

Besides the only vague statements concerning the transdermal therapeutical systems, none of both publications deal with the instability of physostigmine which was realized very early (Eber, W., Pharmaz. Ztg. 37, 483 (1888); Herzig, J., Mayer, H., Mh. Chem 18, 379 (1897); Herzig, J., Lieb, H., ibidem 39, 285 (1918); Solvay, A. A., J. chem. Soc. (London) 101, 978 (1912); instability due to a rapid decomposition extremely limits the use of physostigmine in pharmacy).

Thus it is the object of the present invention to provide physostigmine or one of its pharmaceutically acceptable salts in the form of a transdermal therapeutical system which provides the controlled release of physostigmine or its pharmaceutically acceptable salt over a period of 24 hours and guarantees that the physostigmine does not notably decompose during the storage of the pre-fabricated transdermal therapeutical system.

This object is achieved in that physostigmine is dissolved at least 25% in a solvent or solvent mixture, respectively, which has to be physiologically acceptable, since it is to be expected that both physostigmine and the solvent will migrate through the matrix. Said solvent may be printed onto a textile fabric which has previously been applied to a matrix, said matrix being provided with a protective layer which is impermeable to active substances and optionally rendered removable, by using a printing method, e.g., as described in DE-OS 36 29 304. Subsequently, the printed textile fabric and the matrix are covered with a prefabricated cover layer which is impermeable to active substances as well. With a suitable punching tool the area of which is round and considerably larger than that of the nonwoven fabric it is punched centrically. The adhesive edge which is free of active substance is separated off. This process is known in principle and described in DE-OS 36 29 304. However, in the above mentioned publication nicotine base is the substance in the example; since nicotine base is liquid at room temperature, this process could not simply be adapted. What is more, physostigmine base had to be brought into a high-percentage, i.e., at least 25%, solution, since the singular dosage of powdery components in fact is known in the technology of solid pharmaceuticals, however completely unknown in the technology of semi-solid pharmaceuticals, since this question has not occured until now. At the same time the solvent has to meet three important requirements:

- It must not decompose the physostigmine which is highly instable
- It has to be physiologically acceptable
- It must make it possible that the physostigmine is extremely well soluble during the production of the system, but very badly soluble during storage.

Carboxylic acids having more than ten carbon atoms meet these requirements. When physostigmine is mixed with these compounds both solubilization and formation of salt occur. However, in principle those preparations are liquid at room temperature.

The solubility of the active substance within the matrix is reduced (thus achieving a sufficient release) in that a high content of a basic polymer, for example, a copolymer with cationic character on the basis of dimethylaminoethyl methacrylate and other neutral methacrylic acids, is incorporated into the matrix. Thus, after applying the matrix, an acid-base-reaction occurs between the carboxylic acid and the basic polymer, whereby the solubility of the active substance is considerably reduced. According to the releases of the preparation examples it can be shown that the release rate increases with increasing portion of the basic polymer in the matrix.

In the following the schematic structure of the system is explained.

The cover layer (4) may consist of flexible or inflexible material and may be single or multi-layered. Substances suitable for its production are polymeric substances, for example, polyethylene, polypropylene, polyethylene terephthalate, polyamide. Further materials may be metal foils, such as aluminium foil alone or coated with a polymeric substrate ((5) in the latter case). Textile fabrics may be used as well, if the components of the reservoir, due to their physical properties, cannot penetrate through the textile material. According to a preferred embodiment the covering layer (4) is a composite material Which strengthens the laminate, and serves as barrier against the loss of laminate components. Furthermore, foils vapourized with aluminium or composite materials are suitable.

Matrix (1) adjoins the cover layer. During the fourteen-day storage physostigmine releases from the active substance deposit (2) into the matrix (1) and saturates it so that the matrix becomes a reservoir layer. The matrix has the property to guarantee the coherence of the system. The matrix consists of a basic polymer and optionally of common additives. The selection of the basic polymer depends on the chemical and physical properties of the physostigmine. Examples of polymers are rubber, rubber-like synthetic homopolymers, copolymers or block polymers, polyacrylic acid esters and their copolymers. In principle all polymers are suitable which are used in the production of pressure-sensitive adhesives, which are physiologically acceptable and do not decompose physostigmine. It is particularly preferred to use those polymers consisting of block copolymers on the basis of styrene and 1,3-dienes, polyisobutylenes, or polymers of acrylate and/or methacrylate. In particular, linear styrene-isoprene block copolymers are used from the group of block copolymers on the basis of styrene and 1,3-dienes.

Acrylate-copolymers of 2-ethylhexylacrylate, vinyl acetate, and acrylic acid with or without titane chelate ester are preferred as polymers on acrylate basis. Copolymers on the basis of dimethylaminoethyl methacrylates and neutral methacrylic acid esters are preferred as methacrylates. As esters of hydrogenated colophonium its methyl and glyceryl esters are particularly preferred.

The kind of possible additive depends on the polymer used and the active substance: According to their function they can be divided into softeners, tackifiers, stabilizers, carriers, diffusion and penetration regulating additives or fillers. Suitable physiologically acceptable substances are known to the man skilled in the art. The reservoir layer exhibits such a self-adhesiveness that a constant contact to the skin is guaranteed.

Examples for suitable softeners are diesters of dicarboxylic acids, e.g., di-n-butyl adipate and triglycerides, particularly medium chain triglycerides of the caprylic/capric acid of coconut oil.

The active substance reservoir (2) is positioned between matrix (1) and cover layer (4). It consists of a textile fabric and the physostigmine solution. The textile fabric may be a round blank of nonwoven material (fibre mixture rayon staple/cotton 50:50 having an area weight of 40 g/m² or 80 g/m², respectively) having a diameter of 20–50 mm. Other textiles and other diameters are possible, too.

Higher fatty acids are preferred as compound having at least one acid group, since the extent of possible skin irritations resulting from migrating acids, depends on the chain length of the acids. Examples for suitable acids are oleic acid, isostearic acid, undecenoic acid, and versatic acid.

The removable protective layer, which is in contact with the reservoir layer and is removed prior to application, for example, consists of the same materials as are used for the production of the covering layer (4), provided that they are rendered removable, for example by way of a silicone treatment. Further detachable protective layers, e.g., are polytetrafluoroethylene, treated paper, cellophane, polyvinyl chloride, etc. If the laminate according to the present invention is cut into suitable sizes (plasters) prior to applying the protective layer, the dimensions of the protective layer to be applied may have an overlapping end, so that they may be removed from the plaster more easily.

The following is an explanation of the production:

At first, the matrix (1) is produced, its composition is given in the individual examples for the preparation. After removal of a cover layer, a round nonwoven fabric is applied the area of which is 13.72 cm². A nonwoven having a fibre composition rayon staple/cotton of 70:30, area weight 40 g/m², is used as nonwoven. Subsequently, a rectangular area of 56 cm² is cut from the matrix which is covered with the nonwoven. Nonwoven and matrix are shown in FIGS. 1 and 2. Physostigmine dissolved 25% in oleic acid, or 35% in undecenoic acid is applied to the nonwoven fabric by means of a suitable device, e.g., a dropping pipette. The exact amounts are given in the individual examples for the preparation.

Then active substance deposit (2) and matrix (1) are coverd with a cover layer (4). The cover layer is an adhesive coat consisting of a multi-acrylic copolymer, which has been coated onto a polyester foil 15μ. After removal of the solvent the area weight amounts to 30 g/m². After covering, a round area of 21.23 cm² is punched out so that the nonwoven steeped with active substance solution is positioned centrically (FIGS. 3 and 4). Subsequently, the edges are separated off and the transdermal therapeutical system is stored for 14 days at 40° C.

BRIEF DESCRIPTION OF DRAWINGS

The formation of the system according to the present invention is illustrated in FIGS. 1–4.

Figure 1:
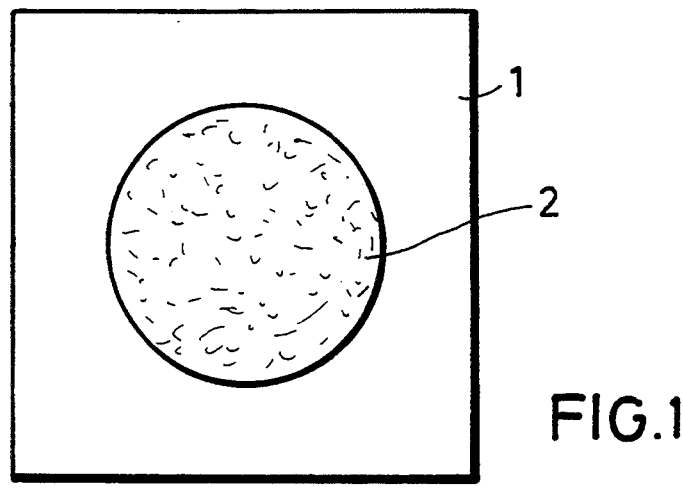
FIG. 1 shows a view of the nonwoven (2) which has been applied to the matrix (1). After applying the nonwoven (2) to the matrix (1), the liquid active substance preparation is applied, whereby the active substance deposit (2) is formed. Subsequently, cover layer (4) is laminated over matrix (1) and active substance deposit (2). Then it is punched. The edges are separated off.
Figure 2:
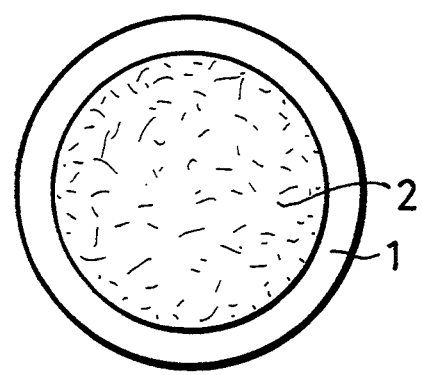
FIGS. 2 and 3 schematically show in top view (FIG. 2) and in side elevation (FIG. 3) active substance deposit (2) positioned on matrix (1) and closing cover (3) after separation.
Figure 3:
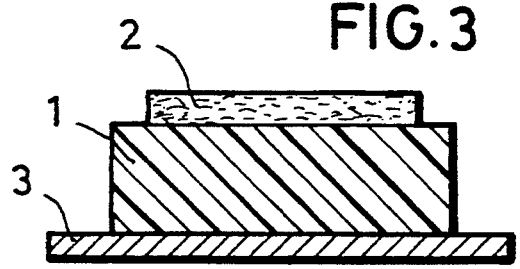
Figure 4:
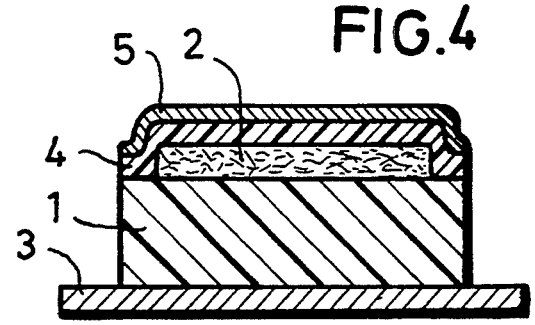

The system is completely shown in FIG. 4 in side elevation. Numbering of FIGS. 1 to 4:

1 matrix
2 active substance deposit or nonwoven, respectively
3 protective layer
4 cover layer
5 metal foil FIG. 5 and 6 show the in vitro release behavior of Example XXX.

EXAMPLES OF PREPARATIONS

Example I

Preparation of the matrix: 10.91 kg of a 40% solution of a self-crosslinking acrylate copolymer of 2-ethylhexyl acrylate, vinyl acetate, and acrylic acid with titane chelate ester, solvent mixture: ethyl acetate, ethanol, heptane, methanol 64:25:9:2 and 2.4 kg of a 50% solution of a cationic copolymer on the basis of dimethylaminoethyl methacrylate and neutral methacrylic acid esters in ethyl acetate, are mixed under stirring at room temperature with 360 g triglycerides of caprylic/capric acids. By means of a suitable coating knife it is coated onto a polyester foil vapourized with aluminium and covered with a LDPE-foil. The area weight shall lie in the range of 260.0 g to 275 g/m².

| Composition of matrix 1: | |
| --- | --- |
| Self-crosslinking acrylate copolymer ACP₁ | 74% |
| Methacrylate copolymer MCP | 20% |

| Composition of matrix 1: | |
|---|---|
| Triglycerides of caprylic/ caperic adids (TriG) | 6% |
| | 100% |

The LDPE-foil is removed and the nonwoven applied. A mixture of 12 mg physostigmine and 36 mg oleic acid is applied on the nonwoven by means of a dropping pipette.

All further examples and example I are listed in the following tables. The in-vitro release was determined in a shaking water bath at 37° C. The acceptor medium was 100 ml physiological saline which was completely exchanged after 2, 4, and 8 hours. The concentrations were determined after 2, 4, 8, and 24 hours by means of UV-spectroscopy.

The release values listed in the tables are the sums of the concentrations measured.

Table 1 shows the construction and the in-vitro release of examples I to IV. In these examples the same matrix was used, however, the coating amount varies; physostigmine dissolved 25% in oleic acid was applied.

It can be recognized that in the case of an increased physostigmine content the absolute as well as the relative release increases.

In examples IV-XXIII each -time 20 mg physostigmine - dissolved in 60 mg oleic acid - are added. The proportional compositions of the matrices and the area weights (AW) were changed. The indications as to the matrices are given in Table 2.

Explanation of the abbreviations used in the tables:

$ACP_1$ : self-crosslinking acrylate copolymer of 2-ethylhexyl acrylate, vinyl acetate, acrylic acid with titane chelate ester as cross-linking agent $ACP_2$ : non-self-crosslinking acrylate copolymer of 2-ethyl-hexyl acrylate, vinyl acetate, and acrylic acid MCP : copolymer on the basis of dimethylaminoethyl meth-acrylate and neutral methacrylates Trig: triglycerides of the caprylic/capric acids K.E.: Ester of the resin acid colophonium with glycerol

TABLE 2

Composition of the matrices and in-vitro release in tabular form

| Example | ACP | MCP | Trig | Additives | AW | 2 h | 4 h | 8 h | 24 h | remarks |
|---|---|---|---|---|---|---|---|---|---|---|
| IV | $ACP_1$:74% | % | 6% | — | 180 g/m² | 6.43 | 9.15 | 12.76 | 17.47 | |
| V | $ACP_1$:76% | 20% | 4% | — | 320 g/m² | 3.58 | 5.06 | 7.14 | 12.16 | |
| VI | $ACP_1$:78% | 20% | 2% | — | 210 g/m² | 5.65 | 8.07 | 11.42 | 17.34 | |
| VII | $ACP_1$:78% | 20% | 2% | — | 310 g/m² | 3.92 | 5.57 | 7.86 | 13.32 | |
| VIII | $ACP_1$:80% | 20% | — | — | 210 g/m² | 4.76 | 6.93 | 10.02 | 16.54 | |
| IX | $ACP_1$:80% | 20% | — | — | 310 g/m² | 4.15 | 5.89 | 8.31 | 13.81 | |
| X | $ACP_1$:86% | 10% | 4% | — | 295 g/m² | 3.06 | 4.41 | 6.39 | 10.82 | |
| XI | $ACP_1$:68.5 | 20% | 4% | K.E.:7.5% | 320 g/m² | 3.16 | 4.45 | 6.31 | 10.40 | |
| XII | $ACP_1$:66% | 20% | 4% | K.E.:10% | 320 g/m² | 3.11 | 4.35 | 6.20 | 10.19 | |
| XIII | $ACP_1$:76% | 10% | 4% | K.E.:10% | 310 g/m² | 2.58 | 3.67 | 5.32 | 8.92 | |
| XIV | $ACP_2$:56% | 30% | 4% | oleic acid:10% | 240 g/m² | 6.35 | 9.49 | 14.91 | 19.89 | |
| XV | $ACP_2$:56% | 30% | 4% | oleic acid:10% | 340 g/m² | 3.70 | 5.48 | 7.77 | 13.43 | |
| XVI | $ACP_2$:46% | 40% | 4% | oleic acid:10% | 240 g/m² | 5.71 | 8.55 | 12.38 | 17.74 | |
| XVII | $ACP_2$:46% | 40% | 4% | oleic acid:10% | 340 g/m² | 2.99 | 4.46 | 6.36 | 11.59 | |
| XVIII | $ACP_1$:69% | 20% | 6% | oleic acid:5% | 230 g/m² | 6.95 | 10.22 | 13.88 | 18.22 | |
| XIX | $ACP_1$:69% | 20% | 6% | oleic acid:5% | 345 g/m² | 4.44 | 6.58 | 9.17 | 14.62 | |
| XX | $ACP_2$:74% | 20% | 6% | — | 195 g/m² | 5.53 | 8.17 | 11.46 | 17.04 | see IV |
| XXI | $ACP_2$:74% | 20% | 6% | — | 290 g/m² | 3.23 | 4.77 | 6.69 | 11.26 | |
| XXII | $ACP_2$:69% | 20% | 6% | oleic acid:5% | 240 g/m² | 5.73 | 8.47 | 11.80 | 17.17 | see XVIII |
| XXIII | $ACP_2$:69% | 20% | 6% | oleic acid:5% | 350 g/m² | 3.55 | 5.22 | 7.32 | 12.31 | |

In the case of examples XXIV-XXXI each time 20 mg physostigmine - mixed with 37 mg undecenoic acid - were added. The proportional compositions of the matrices and the area weights were changed. The indications as to the matrices are given in Table 3.

| Example | ACP | MCP | TriG | Additives | AW | 2 h | 4 h | 8 h | 24 h | remarks |
|---|---|---|---|---|---|---|---|---|---|---|
| XXIV | $ACP_1$:74% | 20% | 6% | — | 200 g/m² | 7.05 | 10.23 | 14.9 | 19.57 | see IV |
| XXV | $ACP_1$:74% | 20% | 6% | — | 295 g/m² | 4.48 | 6.48 | 9.32 | 15.84 | |
| XXVI | $ACP_1$:80% | 20% | — | — | 195 g/m² | 5.97 | 8.89 | 13.16 | 19.13 | see VIII |
| XXVII | $ACP_1$:66% | 20% | — | — | 295 g/m² | 4.00 | 5.92 | 8.7 | 15.24 | see IX |
| XXVIII | $ACP_1$:66% | 20% | 4% | K.E.:10% | 210 g/m² | 5.88 | 8.84 | 13.33 | 18.94 | |
| XXIX | $ACP_1$:66% | 20% | 4% | K.E.:10% | 305 g/m² | 3.80 | 5.60 | 8.31 | 15.06 | see XII |
| XXX | $ACP_1$:86% | 10% | 4% | — | 200 g/m² | 4.65 | 6.72 | 9.61 | 15.90 | |
| XXXI | $ACP_1$:86% | 10% | 4% | — | 295 g/m² | 3.20 | 4.64 | 6.69 | 11.73 | see X |

TABLE 1

| | | | Release (mg) | | | (%) |
|---|---|---|---|---|---|---|
| Example | Physostigmine | AW | 2 h | 4 h | 8 h | 24 h | 24 h |
| I | 12 mg | 260 | 1.64 | 2.28 | 3.17 | 5.62 | 48.8 |
| II | 12 mg | 180 | 3.28 | 4.60 | 6.29 | 9.19 | 76.6 |
| III | 16 mg | 260 | 2.77 | 4.03 | 6.71 | 10.38 | 56.1 |
| IV | 20 mg | 180 | 6.43 | 9.15 | 12.76 | 17.47 | 87.4 |

AW = Area weight of the matrices (g/m²)

FIGS. 5 and 6 show the in-vitro release behaviour of example XXX which had been chosen at random. Since the released amount calculated against the root of time - as is the case in almost all of the examples - result in a straight line, it can be shown that systems have been developed which release the active substance in a controlled manner via the matrix, since the requirements of the Higuchi-model are clearly met.

It turns out that the release is determined by the molar ratio of the carboxylic acids to the basic polymer. It can be proved that the release is the higher the less acid and the more basic polymer had been incorporated. The release is the higher the less undissociated acid is present in the systems after storage. Since in molar amounts less undecenoic acid has been used in contrast to oleic acid, it can be understood why the samples containing undecenoic acid release more of the physostigmine than those containing oleic acid both having the same matrix. It can be demonstrated by graduation of the softener that the softener does not influence the in-vitro release.

We claim:

1. A transdermal therapeutic system for the administration of physostigmine to the skin comprising a cover layer which is impermeable to active substances, a pressure-sensitive adhesive reservoir layer, the reservoir layer comprising 10–19%-wt material selected from the group consisting of block copolymers on the basis of styrene and 1,3-dienes, polyisobutylenes, polymers on the basis of acrylate and/or methacrylate and esters of hydrogenated colophonium, the polymeric material being rendered basic by a basic polymer, whereby the solubility of the physostigmine is reduced, 0–30%-wt softener on the basis of hydrocarbons and/or esters, the active substance deposit immediately after production comprising 15–85%-wt of a 0.1–70%-wt physostigmine solution, in a solvent with at least one acidic group.

2. The transdermal therapeutic system according to claim 1, wherein the reservoir layer material comprises a self-crosslinking acrylate copolymer of 2-ethylhexylacrylate, vinyl acetate, acrylic acid and titane chelate ester.

3. The transdermal therapeutic system according to claim 1, wherein the reservoir layer material comprises a non-self-crosslinking acrylate copolymer of 2-ethylhexylacrylate, vinyl acetate and acrylic acid.

4. The transdermal therapeutic system according to claim 1, wherein the reservoir layer material comprises a polymer on the basis of a methacrylate, a copolymer on the basis of dimethylaminoethyl methacrylate and a neutral methacrylic acid ester.

5. The transdermal therapeutic system according to claim 1, wherein the reservoir layer material comprises as ester of the hydrogenated colophonium its methyl ester.

6. The transdermal therapeutic system according to claim 1, wherein the reservoir layer material comprises as ester of the hydrogenated colophonium its glycerol ester.

7. The transdermal therapeutic system according to claim 1, wherein the reservoir layer comprises as softener dioctylcyclohexane.

8. The transdermal therapeutic system according to claim 1, wherein the reservoir layer comprises as softener di-n-butyl adipate.

9. The transdermal therapeutic system according to claim 1, wherein the reservoir layer comprises as softener a triglyceride.

10. The transdermal therapeutic system according to claim 1, wherein the reservoir layer comprises as softener isopropylmyristate.

11. The transdermal therapeutic system according to claim 1, wherein the compound comprising at least one acidic group is a carboxylic acid.

12. The transdermal therapeutic system according to claim 11, wherein the carboxylic acid comprises oleic acid or undecenoic acid.

13. The transdermal therapeutic system according to claim 11, wherein the carboxylic acid comprises a mixture of octadecane acids.

14. The transdermal therapeutic system according to claim 11, wherein the carboxylic acid comprises versatic acids.

15. The transdermal therapeutic system according to claim 1, further including a removable protective layer.

* * * * *

UNITED STATES PATENT AND TRADEMARK OFFICE
CERTIFICATE OF CORRECTION

PATENT NO. : 5,391,375
DATED : February 21, 1995
INVENTOR(S) : Hille, et al.

It is certified that error appears in the above-identified patent and that said Letters Patent is hereby corrected as shown below:

Title Page       [63] Related U.S. Application Data: After " 727,324 " delete " Mar. 3, 1991 " and substitute -- Jul. 3, 1991 --

Col. 7, line 20  After " 10- " delete " 19% " and substitute -- 90% --

Signed and Sealed this

Thirtieth Day of May, 1995

Attest:

BRUCE LEHMAN

Attesting Officer        Commissioner of Patents and Trademarks